United States Patent
Kodsi

(10) Patent No.: US 8,003,118 B2
(45) Date of Patent: Aug. 23, 2011

(54) USE OF RIFAXIMIN FOR THE PREVENTION OF ASPIRATION PNEUMONIA AND/OR SEPSIS

(76) Inventor: Robert E. Kodsi, Brooklyn, NY (US)

( * ) Notice: Subject to any disclaimer, the term of this patent is extended or adjusted under 35 U.S.C. 154(b) by 1099 days.

(21) Appl. No.: 11/365,430

(22) Filed: Mar. 1, 2006

(65) Prior Publication Data

US 2006/0210592 A1 Sep. 21, 2006

Related U.S. Application Data

(60) Provisional application No. 60/657,748, filed on Mar. 2, 2005.

(51) Int. Cl.
*A61K 31/496* (2006.01)
*A61K 9/00* (2006.01)
*A61K 9/48* (2006.01)
*A61K 9/20* (2006.01)

(52) U.S. Cl. .................. 424/400; 424/451; 424/464

(58) Field of Classification Search .................. None
See application file for complete search history.

(56) References Cited

U.S. PATENT DOCUMENTS

| | | | |
|---|---|---|---|
| 4,341,785 A | 7/1982 | Marchi et al. | |
| 4,557,866 A | 12/1985 | Cannata et al. | |
| 5,314,904 A | 5/1994 | Egidio et al. | |
| 5,352,679 A | 10/1994 | Ferrieri et al. | |
| 5,886,002 A | 3/1999 | Ferrari et al. | |
| 6,140,355 A | 10/2000 | Egidio et al. | |

OTHER PUBLICATIONS

Doson et al. The Annals of Pharmacotherapy. 2007; 41 (4): 647-52, abstract only.*
Hunter et al. European Journal of Anaesthesiology. 2007; 24: 971-977.*
Definition of "sepsis", provided by Stedman's medical dictionary, 27th edition (online), 2005 copyright.*
Drugdex Drug Evaluations for Rifaximin; MICROMEDEX® Healthcare Series (Sep. 2004).
"Spectroscopic Investigation of the Conformational Properties and Self-Association Behavior of Natural Compounds in Solution" published in Spectroscopy Letters, vol. 35, Issue 4 Aug. 14, 2002.
News Article titled "Salix Pharmaceuticals' New Drug Application for LUMENAX Rifaximin for the Treatment of Travelers Diarrhea Accepted for Filing by FDA", Business Editors and Health/Medical Writers Feb. 25, 2002.
www.drugs.com webpage for Xifaxan® (Salix Pharmaceuticals' trade name for Rifaximin®) and consumer questions; revision date Jun. 7, 2004.
Listing from www.rxlist.com stating chemical name and empirical formula for Xifaxan® printed Feb. 7, 2005.
Listing from FDA website (www.fda.gov) regarding XIFAXAN® stating general information about drug; posted Aug. 12, 2004.
Information regarding Xifaxan from the Salix Pharmaceutical's website and results of a study which suggested potential use of Xifaxan in the prevention of Shigellosis Nov. 9, 2004.
XIFAXAN™ datasheet from Salix Pharmaceuticals Inc, NC, Jun. 2004.
www.buy-online-prescription.com listing for the trade name Rifaximine printed Feb. 9, 2005.
www.buy-online-prescription.com listing for trade name Normix printed Feb. 9, 2005.
www.buy-online-prescription.com listing for trade name Flonorm printed Feb. 9, 2005.
www.buy-online-prescription.com listing for trade name Redactiv printed Feb. 9, 2005.
Sheet from www.healthatoz.com with general info about Traveler's Diarrhea and use of Normix to treat it; printed Feb. 9, 2005.
Article titled "Revenge on Montezuma's Revenge," Health Day News printed Feb. 8, 2005.
Brief description of a preliminary study done with Rifaximin from University of Bologna, J Int Med Res. Jul.-Aug. 1988 16(4).
Article titled "Enteroaggregative *Escherichia coli* Diarrhea in Travelers: Response to Rifaximin Therapy," Clinical Gastroenterology and Hepatology vol. 2, No. 2 Feb. 2004.
Article titled "Therapy of Travelers' Diarrhea With Rifaximin on Various Continents," The American Journal of Gastroenterology vol. 98 No. 5 May 2003.
Chapter 38 from Merck Manual regarding Pneumonia p. 681-691, Mar. 1999.
Definition of Pneumonia from www.wikipedia.org printed Feb. 10, 2005.

* cited by examiner

*Primary Examiner* — Shanon A Foley
(74) *Attorney, Agent, or Firm* — Dara L. Onofrio, Esq.; Onofrio Law

(57) ABSTRACT

An oral preparation consisting of a non-systemic antibiotic and a proton pump blocker used for prevention of aspiration pneumonia and sepsis; and a method of prevention of aspiration pneumonia and/or sepsis by orally administering to a subject in need of such treatment a composition containing a therapeutically effective amount of rifaximin.

14 Claims, 1 Drawing Sheet

USE OF RIFAXIMIN FOR THE PREVENTION OF ASPIRATION PNEUMONIA AND/OR SEPSIS

This application claims the benefit of U.S. provisional application No. 60/657,748 filed Mar. 2, 2005 which is incorporated herein in its entirety by reference.

FIELD OF THE INVENTION

This invention relates to use of rifaximin compositions in the prevention of aspiration pneumonia and/or sepsis. More particularly it relates to the use of rifaximin for the prevention of aspiration pneumonia and/or sepsis in patients undergoing acid suppression or undergoing artificial enteral feedings via a Gastrostomy/Jejunostomy or naso/oro gastric tubes. In addition, it relates to prevention of aspiration pneumonia in patients with impairment of mental status for any reason but particularly patients undergoing anesthesia or mechanical ventilation that are at high risk for aspiration pneumonia.

BACKGROUND OF THE INVENTION

In general, rifaximin is well known as a non-systemic antibiotic (<0.4%) characterized by activity against a broad spectrum of enteric bacterial pathogens and the delivery of high concentrations of antibiotic to the gastrointestinal tract.

The antibiotic rifaximin was discovered in 1980 and originally patented in Italy as IT Patent 1154655 granted on Jan. 21, 1987. The related U.S. Pat. No. 4,341,785 to Marchi et al. discloses imidazo-rifamicyn derivatives having antibacterial utility, and the related process for preparing it. The '785 patent also discloses a pharmaceutical antibacterial composition and a method of using it to treat antibacterial diseases of the gastrointestinal tract. A further patent, U.S. Pat. No. 4,557,866 to Cannata et al. discloses a process for the synthesis of pyrido-imidazo rifamycins. The process is described as an improvement over the '785 patent to Marchi in that the later process provides unsatisfactory yields from an industrial point of view.

Rifaximin is essentially a non-absorbable semi-synthetic antibiotic, related to rifamycin. The antimicrobial spectrum (in vitro) includes most gram-positive and gram-negative bacteria; and both aerobes and anaerobes.

It presents low risk for drug interactions (no effect on drugs metabolized by cytochrome p450 enzyme system) and about the same adverse properties as compared to a placebo. When ingested in tablet or pill form rifaximin is concentrated in the gastrointestinal tract and primarily excreted unchanged in the feces. It binds to the beta subunit of bacterial DNA-dependent RNA polymerase, which inhibits bacterial RNA synthesis. In contrast with other antibiotics, resistance to rifaximin is not plasmid-mediated but utilizes a chromosomal one-step alteration in the DNA-dependent RNA polymerase. In subjects using rifaximin no relevant resistance has been observed. Further, mutant resistant bacteria showed reduced viability and there is no systemic cross resistance for rifampin.

Since rifaximin is practically insoluble in water and is non absorbed (<0.4%) after oral administration, it can be used to treat localized diseases of the gastrointestinal tract. Rifaximin products specific for enteric pathogens of the gastro-intestinal tract are presently commercially marketed under various trade names—NORMIX® available from Alfa Wassermann S.p.A., Bologna, Italy; XIFAXAN® available from Salix Pharmaceutical, Raleigh, N.C.; REDACTIV® available from GlaxoSmithKline and FLONORM® from Schering-Plough. Since the solubility of rifaximin in water is approximately 1 $\mu g m L^3$ the drug is virtually undissolved when traveling through the GI tract. The relative insolubility of rifaximin is thought to influence bacterial susceptibility and subsequent eradication due to the invasive nature of some enteric pathogens (e.g. *Salmonella* and *Campylobacter*). The relative insolubility of rifaximin also leads to its negligible systemic absorption. Rifaximin has been known to be effective for treating infections that are localized to the gut and is not known to be suitable for treating systemic infections caused by invasive organisms.

Rifaximin has been marketed in Italy since 1985 under the trademark NORMIX® for treating acute and chronic intestinal infections from gram-positive and gram-negative bacteria and as adjuvant in the therapy of the hyperammonoaemia. At present NORMIX® is marketed in the shape of pharmaceutical compositions, orally administrable, made by tablets or by granulates containing suitable pharmaceutically acceptable excipients together with rifaximin, but also other pharmaceutical forms orally administrable like capsules, sugar coated tablets and syrups can be used.

Xifaxan® is marketed in the United States and Canada and includes rifaximin as the active ingredient. The formulation is used in the treatment of travelers' diarrhea caused by the noninvasive strains of *Escherichia coli*. Xifaxan® is a non absorbable antibiotic for gastrointestinal infections. Dr. Herbert DuPont, director of the Center for Infectious Diseases at the University of Texas, School of Public Health developed the drug for treatment of travelers' diarrhea. DuPont said "the drug is unique in that it remains in the gastrointestinal tract, compared with powerful antibiotics like Cipro that disperse throughout the body. This means the drug is less likely to breed resistant bacteria." He said the antibiotic proved 85% effective in protecting US students who participated in a two-week study trip to Mexico, versus just 49% who didn't become sick on non-medicinal placebos. The drug has been found to have no significant side effects.

Products similar to NORMIX® and Xifaxan® are marketed in Mexico under the tradenames REDACTIV® and FLONORM®.

Other uses of rifaximin are disclosed in the following patents:

U.S. Pat. No. 5,886,002 to Ferrieri et al. describes use of rifaximin compositions in the treatment of diarrhea from cryptosporidiosis.

U.S. Pat. No. 5,352,679 to Ferrieri et al. describes use of rifaximin (INN) in formulations for treatment of gastric dyspepsia caused by *Helicobacter pylori* bacteria.

U.S. Pat. Nos. 5,314,904 and 6,140,355 both to Egidio et al. disclose compositions containing rifaximin for treatment of vaginal infections.

Known therapeutic uses of rifaximin, administered in a tablet form, include *Clostridum difficile*-associated diarrhea, Crohn's disease, Diverticular disease, Hepatic encephalopathy, *Helicobacter pylori* eradication, infectious diarrhea, irritable bowel syndrome, pouchitis, prophylaxis for GI surgery, small bowel overgrowth, traveler's diarrhea and ulcerative colitis. These therapies are directed to pediatric, adult and elderly subjects.

At present rifaximin has been studied and marketed only for the treatment of some kinds of bacterial infections located in the gastro-intestinal and reproductive tracts however prevention of aspiration pneumonia and sepsis has never been investigated.

Aspiration pneumonia is a lung infection/injury caused by aspiration of bacterial contents with or without chemical injury by gastric contents including acid or bile.

Pneumonia is a lung infection that can be caused by different types of microorganisms including bacteria, viruses, fungi, and parasites. Aspiration pneumonia is a lung infection/injury caused by aspiration of bacterial contents with or without chemical injury by gastric contents including acid or bile. Sepsis is a severe illness caused by overwhelming infection of the bloodstream by toxin-producing bacteria.

It has long been known that hospitalized patients, most significantly in intensive care unit settings, under acid suppression are at high risk for developing pneumonia due to bacterial colonization of the usually near sterile environments of the stomach and proximal small bowel. Critically ill patients are usually placed on acid suppression to prevent gastrointestinal bleeding from ulceration that occurs due to the stress of illness. The bacterial aggregation occurs primarily due to the loss of the acid in the stomach that normally protects the gut from bacteria, and/or the elevation of the pH of the stomach by continuous enteral feeding via nasogastric (NG) tubes or percutaneous endoscopic gastrotomy (PEG) or percutaneous endoscopic jejunostomy (PEJ) tubes. As a result, translocation of bacteria through the gut wall or direct reflux (aspiration) of the bacterial contents into the lung may occur, leading to pneumonia or sepsis.

It has also been recognized that healthy patients on strong acid suppression such as proton pump blockers or H2 blockers are at elevated risk for aspiration pneumonia, likely due to reflux and aspirations of gastric contents that contain elevated amounts of bacteria due to the acid suppression.

It has also been recognized that patients with impaired mental status especially patients undergoing sedation or anesthesia are at increased risk for aspiration pneumonia due to the loss of the protective gag reflux. As acid suppression is given to these patients to prevent chemical (acid) induced pneumonia the risks of bacterial pneumonia have increased.

PRILOSEC®, NEXIUM®, PREVACID®, PROTONIX®, ACIPHEX®, ZEGERID® are examples of commercially available proton pump blockers. Examples of commercially available H-2 BLOCKERS are ZANTAC®, TAGAMENT® and PEPCID®.

Antibiotics, such as rifaximin, that are non-absorbed by the body, have not been used to prevent a systemic illness such as pneumonia or sepsis. The present invention provides advantage in doing so such that there are no systemic side effects. The invention preparations which contain rifaximin directly target the cause of the pneumonia or sepsis without causing systemic harm to the person.

In addition, rifaximin is an antibiotic with a broad spectrum of in vitro bactericidal activity, and as resistance is not mediated through plasmids, it is not transferable to other bacteria in the hospital setting. If resistance did develop, the bacteria would be substantially less able to become pathogenic as they could not produce the RNA dependent proteins as effectively.

The non-absorbed antibiotic substantially reduces the degree of oral and upper gastrointestinal tract bacterial colonization, thus reducing the incidence of pneumonia and sepsis without inducing the complications and side effects a systemic antibiotic would have.

Accordingly the present invention is directed to use of rifaximin in preparations to prevent aspiration pneumonia and sepsis. The invention preparations are preferably provided for patients who have the normal protective mechanisms of the gut compromised by acid suppression or enteral feeding.

It is a general object of the invention to prevent aspiration pneumonia and or sepsis in patients under acid suppression by any type of antacids.

A further specific object of the invention is to prevent aspiration pneumonia and or sepsis in patients under acid suppression by proton pump blockers or H-2 blockers.

Another general object of the invention is to prevent aspiration pneumonia and or sepsis in patients on artificial enteral feeding tubes from developing these diseases.

Another specific object of the invention is to prevent aspiration pneumonia and or sepsis in patients on naso/oro gastric (NG) tubes or percutaneous endoscopic gastrotomy (PEG) or percutaneous endoscopic jejunostomy (PEJ) tubes.

Another specific object of the invention is to prevent aspiration pneumonia and/or sepsis in patients with impaired mental status, most specifically in those patients undergoing sedation or anesthesia.

SUMMARY OF THE INVENTION

The present invention provides a method of preventing aspiration pneumonia and/or sepsis caused by bacteria which consists of orally administering to a subject in need of such treatment a composition containing a therapeutically effective amount of rifaximin.

The invention method and treatments are effective against pneumonia and sepsis that are caused by bacteria. However, they are also believed to be effective against conditions which are caused by protozoa, mycobacterium, RNA dependent viruses, reverse transcriptase dependent viruses and any other infections etiology that utilizes RNA.

The composition is preferably a pharmaceutical composition.

Electrolytic reduction of rifaximin produces a slightly different structure referred to as rifaximin OR (open ring). As used in the specification herein, when the term rifaximin is used it is intended to also include the rifaximin OR structure unless otherwise stated. It is believed that the two molecules are similar in structure but have different chemical properties in solution.

In general, in the compositions of the invention, the therapeutically effective amount of rifaximin delivers a dosage to achieve a concentration of up to 10,000 or more μg/ml per application. It is believed that dosages in the concentration range between 1-1000 μg/ml per application would also be effective. The rifaximin preparations work on the surfaces to which they are exposed with essentially no absorption into the tissue itself. The duration of treatments with the invention formulations can be at daily, weekly or monthly intervals depending on the individual and the desired outcome The composition can be tablets, pills, capsules, sugar coated tablets and syrups, which are taken orally.

Rifaximin as a powder or solid granular form can be used in this form or is incorporated into a liquid preparation. Since the rifaximin essentially is non-reactive, it can be incorporated into aqueous or non-aqueous formulations without losing its efficacy.

The composition can also be a dispersable or disintegrating tablet or impregnated in a mouth swab.

The invention also provides a method of prevention of aspiration pneumonia and sepsis caused by bacteria which consists of enterally administering to a subject in need of such treatment a composition containing a therapeutically effective amount of rifaximin.

The composition is preferably a liquid preparation and maybe further combined with an enteral feeding preparation.

In another embodiment, an oral preparation consisting of a non-systemic antibiotic and a proton pump blocker is provided that is used for prevention of aspiration pneumonia and sepsis. Rifaximin is preferably used, although other non-systemic antibiotics can be used and are within the scope of the invention.

In yet another embodiment, an oral preparation consisting of a non-systemic antibiotic and a H-2 blocker is provided that is used for prevention of aspiration pneumonia and sepsis. Rifaximin is preferably used, although other non-systemic antibiotics can be used and are within the scope of the invention.

Although this disclosure is directed to the preferred use of rifaximin, it is also within the scope of the invention that any non-systemic antibiotic can be included in the compositions and are included herein.

Other objects, features and advantages of the present invention will be apparent when the detailed description of the preferred embodiments of the invention are considered with reference to the drawings, which should be construed in an illustrative and not limiting sense as follows:

DETAILED DESCRIPTION OF THE INVENTION

Figure 1:
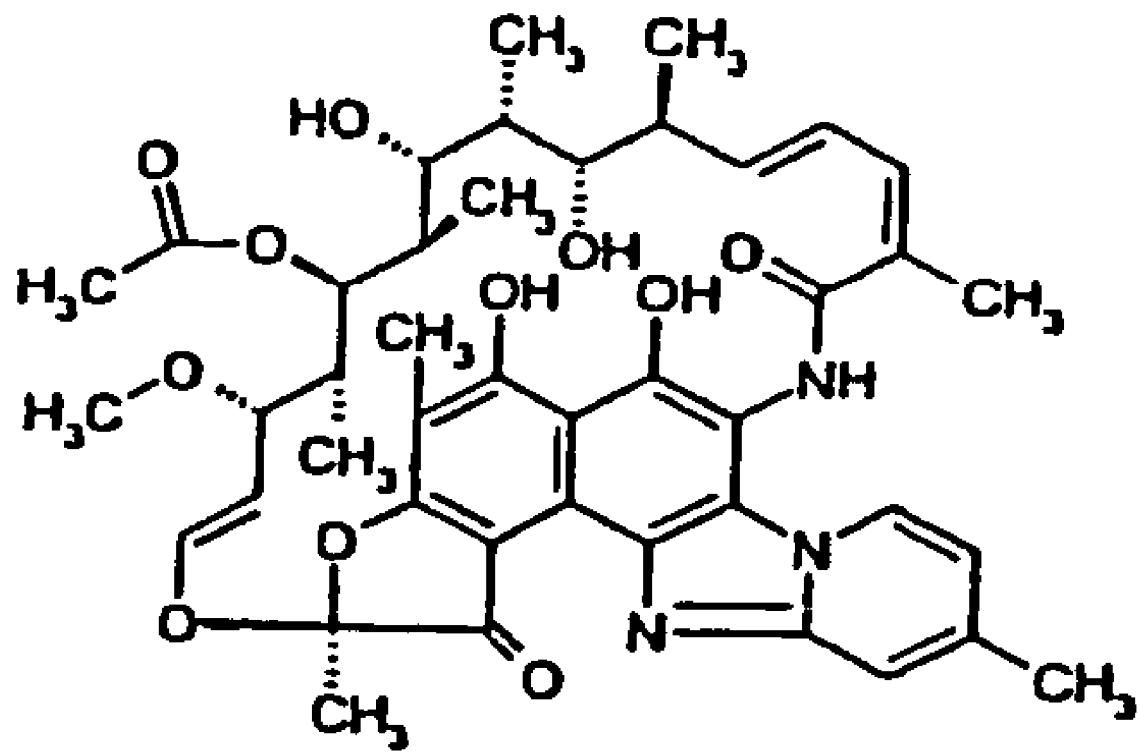
FIG. 1 is the chemical structure of rifaximin.

In general pneumonia is defined as an acute infection of lung parenchyma including alveolar spaces and interstitial tissue; involvement may be confined to an entire lobe (lobar pneumonia), a segment of a lobe (segmental or lobular pneumonia), alveoli contiguous to bronchi (bronchopneumonia) or interstitial tissue (interstitial pneumonia). These distinctions are generally based on x-ray observations. The etiology and the epidemiology are discussed—such as the types of bacteria responsible for pneumonia, predisposing factors and statistics involved with pneumonia There are various types of pneumonia such as Pneumococcal Pneumonia, Staphylococcal Pneumonia, Streptococcal Pneumonia, pneumonia caused by Klebsiella Pneumoniae and other Gram-Negative Bacilli, pneumonia caused by Hemophilus Influenzae, Pneumonia of Legionnaries' Disease, Mycoplasmal Pneumonia, and Chylamydial Pneumonia Pneumonia occurs in patients all age groups, but young children and the elderly, as well as immunocompromised and immune deficient patients, are especially at risk. Casual therapy is with systemic antibiotics.

Sepsis is a systemic response to infection, which causes organ failure and death in severe cases; however, early diagnosis and appropriate treatment can greatly improve survival rates. Current treatment options include anti-infectives and source control.

The more critical subsets of sepsis include severe sepsis (sepsis with organ dysfunction) and septic shock (sepsis with refractory arterial hypotension).

The systemic inflammatory response syndrome leads to widespread activation of inflammation and coagulation pathways. This may progress to dysfunction of the circulatory system and, even under optimal treatment, multiple organ dysfunction syndrome and eventually death. Sepsis is more common and also is more dangerous in elderly, immunocompromised, and critically ill patients.

Current treatments for Reflux Disease are divided into four groups of medication that have different effects. In order of increasing effectiveness these are products that provide protection from gastric acid such Antacids (Alucol, Rennie, Ulcogant, etc.), products that inhibit acid production known as H2 receptor blockers (Zantac), prokinetic products that stimulate evacuation of the stomach (Prepulsid) and proton pump blockers (Nexium).

The present invention, in contrast to known methods, provides a method of prevention of aspiration pneumonia and sepsis caused by bacteria. It consists of orally administering to a subject in need of such treatment a composition containing a therapeutically effective amount of rifaximin.

The therapeutically effective amount of rifaximin is preferably 200 mg per application.

Rifaximin is a semi-synthetic, non-systemic antibiotic. The chemical name for rifaximin is (2S,16Z,18E,20S,21S, 22R,23R,24R,25S,26S,27S,28E)-5,6,21,23,25-pentahydroxy-27-methoxy-2,4,11,16,20,22,24,26-octamethyl-2,7-(epoxypentadeca-[1,11,13]trienimino)benzofuro[4,5-e] pyrido[1,2-α]-benzimidazole-1,15(2H)-dione,25-acetate.
The empirical formula is $C43H51N3O11$ and its molecular weight is 785.9. The chemical structure is shown in FIG. 1.

Compositions containing a therapeutically effective amount of rifaximin are orally administered to a subject in need of such treatment. The composition is preferably a pharmaceutical composition and contains a therapeutically effective amount of rifaximin which preferably delivers a dosage to achieve a concentration of up to 10,000 or more µg/ml per application. It is believed that dosages in the concentration range between 1-1000 µg/ml per application would also be effective. The duration of treatments with the invention formulations can be from one to three times per day to once a month depending on the individual and the desired outcome.

It is known that 80-90% of orally administered rifaximin is concentrated in the gut with less than 0.01% in other tissues.

As contemplated by the invention, the rifaximin can be delivered to the patient in various forms including, tablet or pill form, oral liquid preparation, disintegrating tablet, mouth swab coupled with an enterally dissolved preparation. These forms are now more particularly described.

In a first embodiment, pharmaceutical compositions, orally administrable, are made by tablets(pills) or by granulates containing suitable pharmaceutically acceptable excipients together with rifaximin. Other pharmaceutical forms orally administrable like capsules, sugar coated tablets and syrups can also be used.

In a second embodiment, an oral liquid preparation containing rifaximin is provided. Rifaximin as a powder or solid granular form is incorporated into a liquid solution. Since the rifaximin is non-reactive, it can be incorporated into any liquid formulation without losing its efficacy. This preparation is a swish and swallows preparation taken by a patient having the ability to swallow medication.

In a third embodiment, an oral distintegrating or dispersable tablet containing rifaximin is provided for patients able to take and swallow medication.

In a fourth embodiment, for patients who are unable to swallow, rifaximin is provided in a mouth swab. For patients undergoing artificial enteral feeding, using PEG, NG, PEJ tubes and the like, an enterally dissolved preparation containing rifaximin is used and may be coupled with the mouth swab.

Depending on the embodiment, the rifaximin preparations are used either on a continuous (i.e. daily, every other day, weekly, etc.) or intermittent basis to patients at risk for pneumonia or sepsis due to being acid suppressed or artificially enteral fed.

In enteral feeding, rifaximin can be administered as described in the fourth embodiment or added to eneral feeding preparations, such as Ensure or others. This would serve the dual purpose of prolonging the time in which it was safe to hang the enteral formula, as well as to allow rifaximin to suppress bacterial overgrowth in the stomach on a continuous basis.

In yet a further embodiment, rifaximin can be combined with a proton pump blocker to form a single tablet combining the acid suppressing properties of the proton pump blocker with the antibacterial effect of rifaximin. Examples, of proton pump blockers which can be used are Omeprazole, Nexium, Prilosec, Prevacid, Aciphex, Protinex or Zegerid, and any other proton pump blockers.

In still another embodiment, rifaximin can be combined with an H-2 blocker to form a single tablet combining the acid suppressing properties of the H-2 blocker with the antibacterial effect of rifaximin. Examples, of H-2 blockers which can be used are Zantac, Tagament, Pepcid and any other H-2 blockers.

The present invention will be illustrated in more detail by the following examples without limiting the scope of the invention in any way.

EXAMPLE 1

200 mg of rifaximin was given to a patient via an enteral route both orally and thru a naso-gastric tube to prevent aspiration pneumonia and sepsis.

EXAMPLE 2

A double blind study to evaluate the efficacy of orally administered rifaximin administered to multiple subsets of patients to prevent aspiration pneumonia and sepsis.

EXAMPLE 3

A trial study in otherwise healthy patients on acid suppression, of varying ages, to evaluate the efficacy of orally administered rifaximin in tablet form, oral liquid preparation and disintegrating/soluble tablet in the prevention of aspiration pneumonia and sepsis.

EXAMPLE 4

A trial study in hospitalized patients at risk for developing pneumonia due to acid suppression or enteral feeding, to evaluate the efficacy of orally administered rifaximin in tablet form, oral liquid preparation, disintegrating/soluble tablet and a mouth swab coupled with enteral feeding in the prevention of aspiration pneumonia and sepsis.

EXAMPLE 5

A trial study to evaluate the efficacy of adding rifaximin to an enteral feeding formulas to find the optimal dose for preventing bacterial overgrowth in the formula and to prevent aspiration pneumonia.

EXAMPLE 6

A trial study to evaluate the efficacy of rifaximin in patients undergoing both elective and emergent, sedation, anesthesia or intubation to find the optimum timing of administering rifaximin to prevent aspiration pneumonia.

The invention now being fully described, it will be apparent to one of ordinary skill in the art that many changes and modifications can be made thereto without departing from the spirit or scope of the invention as set forth herein.

What is claimed is:

1. A method of reducing the incidence of aspiration pneumonia which consists of orally administering to a subject in need of such treatment a composition containing a therapeutically effective amount of rifaximin.

2. A method according to claim 1 wherein the aspiration pneumonia is caused by bacteria.

3. A method according to claim 1 wherein said therapeutically effective amount of rifaximin is 200 mg per application.

4. A method according to claim 1 wherein said composition is selected from tablets, capsules, sugar coated tablets, granulates or syrups.

5. A method according to claim 1 wherein said composition is a liquid preparation.

6. A method according to claim 1 wherein said composition is a dispersable or disintegrating tablet.

7. A method according to claim 1 wherein said composition is impregnated in a mouth swab.

8. A method of reducing the incidence of aspiration pneumonia caused by bacteria which consists of enterally administering to a subject in need of such treatment a composition containing a therapeutically effective amount of rifaximin.

9. A method according to claim 8 wherein said composition is a liquid preparation.

10. A method according to claim 8 wherein said composition is further combined with an enteral feeding preparation.

11. An oral preparation consisting of a non-systemic antibiotic and a proton pump blocker used for reducing the incidence of aspiration pneumonia.

12. The oral preparation according to claim 11 wherein said non-systemic antibiotic rifaximin.

13. An oral preparation consisting of a non-systemic antibiotic and a H-2 blocker used for reducing the incidence of aspiration pneumonia.

14. The oral preparation according to claim 13 wherein said non-systemic antibiotic is rifaximin.

* * * * *